United States Patent [19]

Lincklaen-Arriens et al.

[11] 4,090,170
[45] May 16, 1978

[54] PROCESS AND APPARATUS FOR INVESTIGATING THE ACTIVITY OF A CATHODIC PROTECTION UNIT

[75] Inventors: Jan Lincklaen-Arriens, The Hague; Alfred van Tilburg; Teunis L. van Waart, both of Amsterdam, all of Netherlands

[73] Assignee: Shell Oil Company, Houston, Tex.

[21] Appl. No.: 740,904

[22] Filed: Nov. 11, 1976

[30] Foreign Application Priority Data

Dec. 17, 1975 Netherlands .......................... 7514693

[51] Int. Cl.² ............................................. H04B 11/00
[52] U.S. Cl. ..................................... 340/5 R; 307/95; 340/248 A
[58] Field of Search ................... 340/4 E, 5 R, 248 A, 340/248 B, 248 C, 18 FM; 307/95

[56] References Cited

U.S. PATENT DOCUMENTS

| | | | |
|---|---|---|---|
| 3,133,261 | 5/1964 | Ott | 340/5 R |
| 3,860,912 | 1/1975 | Romans | 340/248 C |
| 3,930,220 | 12/1975 | Shawhan | 340/18 FM |
| 3,953,742 | 4/1976 | Anderson et al. | 307/95 |

Primary Examiner—Richard A. Farley

[57] ABSTRACT

A method and apparatus for remotely measuring the cathodic protection level on a cathodically protected structure. The method uses a remote apparatus to measure the cathodic protection level and convert it to a related acoustic signal that is transmitted via the structure or surrounding media to a conveniently located receiving location.

15 Claims, 4 Drawing Figures

U.S. Patent   May 16, 1978   4,090,170
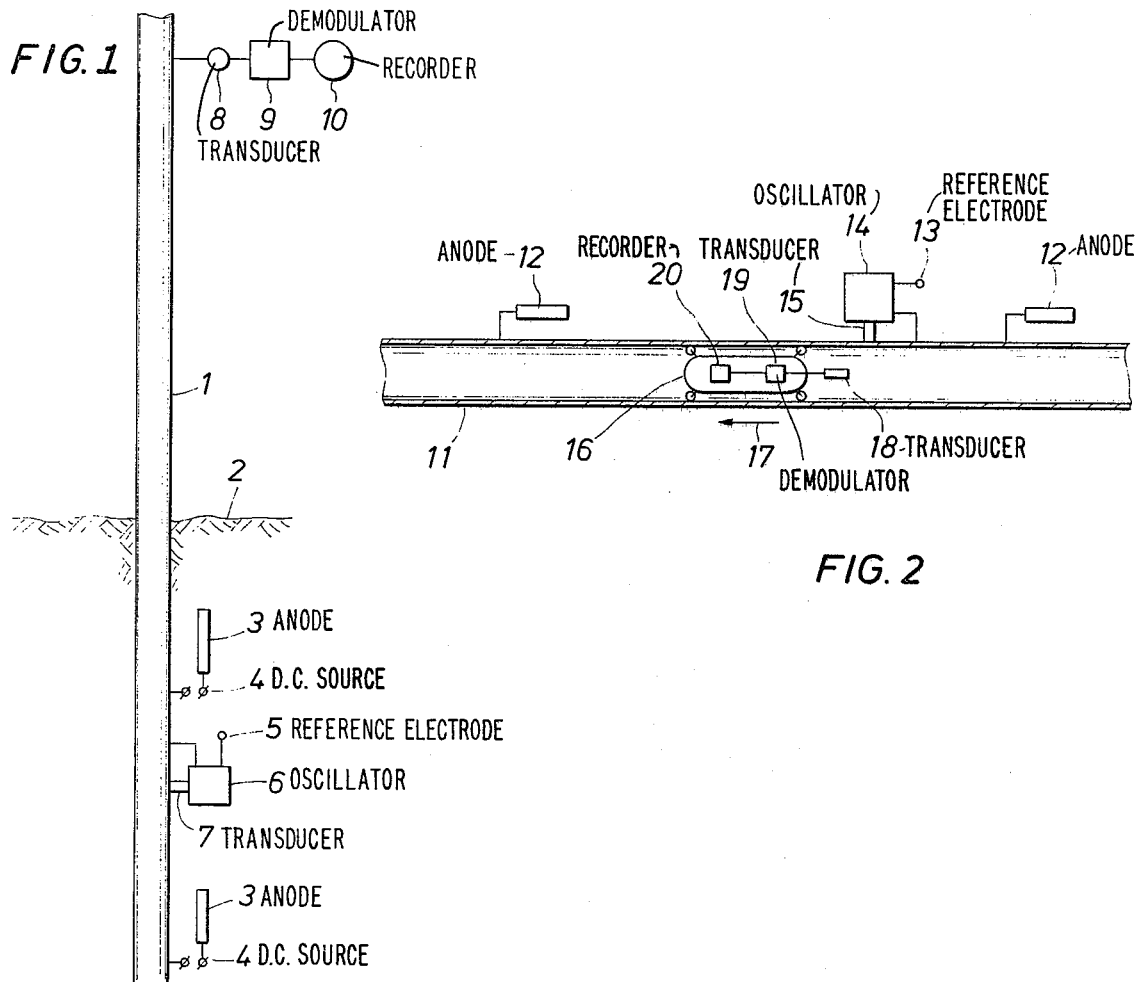
FIG. 1
FIG. 2
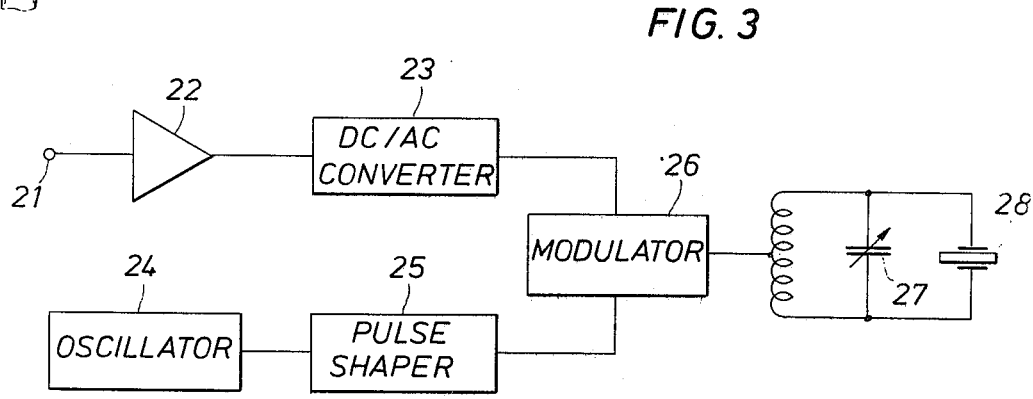
FIG. 3
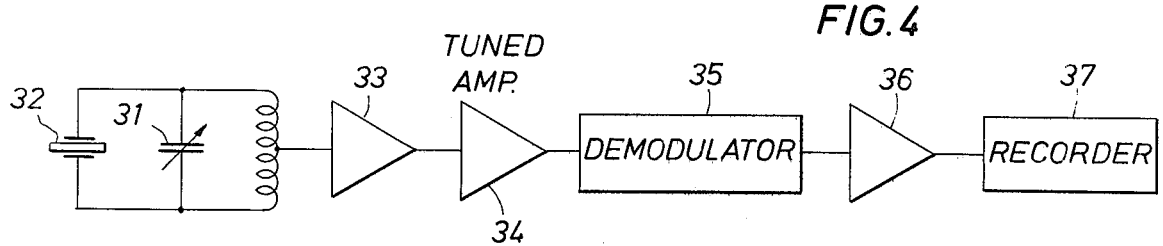
FIG. 4

PROCESS AND APPARATUS FOR INVESTIGATING THE ACTIVITY OF A CATHODIC PROTECTION UNIT

BACKGROUND OF THE INVENTION

The invention relates to a process for investigating the activity of a cathodic protection unit installed on a metal structure that is located under water or in groundwater. The invention further relates to an apparatus suitable for carrying out that process.

Cathodic protection is a method for combating corrosion of metals that are exposed to the action of water. A great variety of constructions, such as pipelines, offshore drilling and production platforms, piers, sluicegates and ships, are protected in this way.

Metal corrosion in an electrolyte at atmospheric temperature is an electrochemical process. At the surface of the corroding metal anodic and cathodic sites develop, whose distribution over the metal surface is dependent on the condition of this surface and is affected by inclusions, oxide layers, etc. The metal of the anodic sites will pass into solution and at the cathodic sites reduction of the oxygen present in the electrolyte place. In the electrolyte an electric current begins to flow from the anodic to the cathodic sites.

The principle of cathodic protection is the prevention of the potential-dependent anodic solution reaction of the metal. This aim is achieved when no current flows through the electrolyte from the anodic to the cathodic sites. A decrease of the potential of the metal from the corrosion potential to the protection potential is obtained by passing the current required for the cathodic reduction reaction from an external source through the electrolyte to the metal, so that this current is no longer supplied by the passing into solution of the metal. Two methods are used for this purpose. In the case of protection by impressed current — active cathodic protection — the object to be protected is coupled to a direct-current source which causes a current to flow via an anode system to the object. The process using sacrificial anodes — passive cathodic protection — is based on the formation of a galvanic cell when the object to be protected is coupled to a less noble metal that acts as the anode and passes into solution, so that at the wall of the object only oxygen reduction occurs.

Passive cathodic protection of steel in seawater may be achieved with magnesium, often alloyed with 6% Al and 3% Zn. Also very suitable anode material is aluminum, often alloyed with 4% Zn and 0.02% In. A sacrificial anode for prolonged use may have a weight of 500 kg. Soft iron is a very suitable anode material for the protection of alloys containing copper.

Whichever the system used, protection is only obtained if a certain current flows through the electrolyte from the anode to the object to be protected. However, in most cases it is not the current density that is chosen as criterion, but the potential relative to a reference electrode, which can be measured more easily. For iron in aerated seawater the protection potential lies somewhere near $-780$ mV. This potential is determined by connecting a voltmeter with a high input impedance to the protected construction and to a reference electrode placed close to it. Reference electrodes may be a calomel, a copper sulphate, a silver chloride, or a hydrogen electrode, but also, for instance, zinc. With large structures, for instance a submarine pipeline, direct measurement of this potential is very cumbersome or even impracticable. Regular checking of the proper functioning of a cathodic protection unit is, however, of great importance in view of the reliability of the structure. The invention indicates how a reliable continuous or at least regular inspection of a cathodic protection unit can be carried out.

BRIEF SUMMARY OF THE INVENTION

The invention therefore relates to a process for investigating the activity of a cathodic protection unit installed on a metal structure that is located, at least partly, under water or in groundwater, the potential difference between a point of the structure and a reference electrode placed in the water in the vicinity of that point being converted into a corresponding acoustic signal, which signal is transmitted to the metal structure or to the surrounding water, from which the signal is picked up for measurement and/or further processing. The acoustic signal may be built up of audible and/or ultrasonic vibrations.

An acoustic signal can be transmitted through metal or water over distances in the tens of meters and be detected with a suitable transducer such as a microphone, a hydrophone, or an accelerometer. So, the invention makes an elegant use of the surrounding medium — water — or the construction material — often steel — to transmit the desired information to a readily accessible place without the necessity of installing long lines for transmitting signals from the points of measurement to the point of observation. These signal lines are always very vulnerable. In the case of large structures the measurements may be centralized. It is then also possible for vulnerable and costly data-processing equipment, such as a computer and a recording device, to be installed in a readily accessible place.

BRIEF DESCRIPTION OF THE DRAWINGS

The invention will now be further elucidated with reference to some figures:

FIG. 1 is a diagrammatic representation of an embodiment of the invention for a steel structure that stands partly in water.

FIG. 2 shows the same as FIG. 1 for a pipeline.

FIG. 3 is a block diagram of an oscillator that can be modulated.

FIG. 4 is a block diagram of a transducer.

PREFERRED EMBODIMENTS

As explained above, the present invention measures the cathodic protection level at a remote point and converts the measurement to an acoustic signal that is transmitted to an observation point. Naturally, the points where the potential is measured may be chosen freely. However, from an economic point of view the number of measurement points should not be too large. Measurements will preferably be taken at critical points in the structure, such as complex geometries where the current distribution is difficult to predict. It is also advisable that the measurement points should be far from the anode, since a slight decline in activity of an anode is noticed sooner at a long distance from that anode than close to it. In certain cases it may be necessary to determine the current density or the rate of current supplied by the anode. In those cases these quantities are converted into a proportional voltage and can be measured in the same way as the protection potential.

The acoustic signal preferably consists of a modulated ultrasonic carrier wave. A suitable carrier frequency is 20–150 kHz, while the modulating signal may have a frequency of 20–1000 Hz. The modulating signal is then the carrier of the measured potential difference. Suitable forms of modulation are frequency modulation, pulse modulation and amplitude modulation. Liquids, in particular water, and metals are very good conductors of ultrasonic vibrations. Receipt of the acoustic signal may take place by tuning observation equipment to the ultrasonic carrier wave, and noise may thus be exluded from the observation.

In the case of measurements being made at more than one point, each measuring unit may supply a coded signal that is characteristic of that unit. It is advantageous for each measuring unit to be given a different carrier wave frequency, so that selection and identification can take place by tuning of the observation equipment. Also, when a single carrier wave frequency is used, the code can be incorporated in the modulating signal. A possibility here is to give each measuring unit a different frequency range for the modulation. If no carrier wave is used, it is also possible for a different frequency range to be chosen for the signal to be supplied by each measuring unit to enable those units to be identified.

When the process according to the invention is applied to an offshore metal structure, either floating or not floating, it is possible for the acoustic signal to be picked up from a structural part above the water level in or near a working space. Such structures are often used in offshore oil or gas drilling and in the production of deposits already struck. They may be fixed structures, but also mobile gravity platforms resting on the sea bottom. Further, there are various types of floating platform whose dimensions are dependent on the water depth. Structures of huge dimensions are dependent on the water depth. Structures of huge dimensions are used and, in many cases, they have a crew on board permanently, although the invention can also be used on unmanned platforms. The signals can be recorded automatically and inspected from time to time. It is also possible for the signals to be transmitted by radio to the coast or to a manned platform.

When the process according to the invention is applied to a ship the acoustic signal is preferably picked up from a structural part on or near the bridge.

Special possibilities arise when the process according to the invention is applied to a submarine pipeline. The acoustic signal may be transmitted to the water and be picked up by a vessel that follows the course of the pipeline. The acoustic signal may also be transmitted to the wall of the pipeline and picked up by a pig that is passed through the pipeline and is provided with equipment for detecting and recording the acoustic signals. This method is suitable particularly for long pipelines. Use may be made here of a pig that is designed for recording and locating acoustic signals from a small leak in a pipeline. The oil issuing under a high pressure from a small leak causes a hissing sound which contains, in addition to audible vibrations, strong ultrasonic vibrations. By turning the equipment present in the pig to a specific ultrasonic frequency the influence of a variety of noise can be eliminated. The pig is carried through the pipeline by the oil stream.

When the pig is used for invertigating the activity of a cathodic protection unit according to the invention, it must be possible for the relevant acoustic signals to be distinguished from the acoustic signals from a leak, if any. This does not present a problem, however, since both in the modulating signal and in the carrier wave there are sufficient degrees of freedom for this aim to be reached.

With pipelines it is of course also possible for the acoustic signals that have been transmitted to the steel pipewall to be picked up from that wall at a suitable place farther on. This is important especially for short pipelines, such as the fixed piece of a line from a mooring buoy suitable for loading and unloading a tanker to the shore.

An apparatus suitable for carrying out the process according to the invention may consist of a reference electrode placed in the water in the vicinity of a measurement point of the structure. The measurement point and reference electrode are connected to the input of an oscillator for generating acoustic vibrations whose frequency is dependent on the potential difference between the measurement point and the reference electrode. The oscillator is provided with an apparatus which through the action of the oscillator can be made to vibrate mechanically at the frequency generated by that oscillator. The vibrating apparatus is in contact with the metal structure or with the water, while a receiving transducer is installed elsewhere against the structure or in the water and connected to an amplifier and a measuring and/or recording unit. The frequency or the frequency range of the vibrations produced can be freely chosen.

A suitable embodiment consists of an oscillator that can generate an ultrasonic carrier wave and that is provided with means for modulating that carrier wave with the vibrations coming from the aforementioned voltage-dependent oscillator. The carrier-wave oscillator operates independently. This oscillator is tuned to a predetermined frequency. When more than one measurement point is used there are as many carrier-wave oscillators as there are measurement points and, naturally, also as many voltage-dependent oscillators. It is then possible for each carrier-wave oscillator to be given a different frequency. At the place of the structure where the signal is picked up there is a transducer which is connected with an amplifier, which amplifier can be tuned to the frequency of the carrier wave. If there are two or more measurement points with different frequencies of the carrier waves, the frequencies detected by the transducer can be scanned by varying the tuning of the amplifier. Naturally, other known techniques, may be applied here as well, such as tuning of the transducer, the use of a frequency read-out circuit in the measuring and/or recording unit, and the use of a computer wih a multiplexer.

At each measurement point a power supply for the electronic equipment is required. Since the measurement points concerned are under water and often, as in the case of pipelines, at great depths spaced over distances in the tens of kilometers, it is important to have longlife power supplies, because the replacement of exhausted power supplies is very expensive. A suitable voltage source is a nuclear cell having a long service life.

When a pig is used in a pipeline, then, to save electric energy, the electronic equipment along the pipeline may normally be switched off and be switched on by the pig only whe it approaches the measurement point. This is important especially when sources of power other than nuclear ones are used, such as galvanic cells. This system of switching on and off may, naturally, also be applied in other installations as discussed hereinbefore.

Referring to FIG. 1, item 1 is a steel structural component, e.g., a part of a leg of an offshore drilling rig. This is partly under the water surface 2. The steel is protected against corrosion by active cathodic protection by means of anodes 3, which, together with the steel component 1, are connected with a direct current source 4.

A reference electrode 5 placed in the water has an electrical connection with a box 6, which box also has an electrical connection with the steel component 1. The box 6 contains a generator of acoustic vibrations, which can be modulated, as will be discussed with reference to FIG. 3. The vibrations generated are transmitted to a crystal 7 that is pressed against the steel component 1. These vibrations hold information about the potential difference between the reference electrode 5 and the steel component.

The vibrations propagate through the steel component 1 and are detected above the water surface 2 by a transducer 8, coupled by an electrical connection to a box 9, which contains components for demodulating the vibrations received (see FIG. 4). A meter and/or recording device 10 records the result of the measurement. The components 8, 9 and 10 are at a readily accessible place.

FIG. 2 shows a part 11 of a submerged pipeline. This pipeline is protected against corrosion by passive cathodic protection, e.g., with the aid of magnesium electrodes 12, which have a galvanic connection with the pipeline 11. Parts 13, 14, 15 correspond respectively to parts 5, 6, 7 in FIG. 1.

A pig 16 can move through the pipeline along with the medium flowing through the pipeline in the direction indicated by arrow 17. On the outside of its rear face the pig 16 carries a transducer 18. This receives acoustic vibrations that have been transmitted by the crystal 15 to the pipeline 11 via the medium in the pipeline. Parts 19 and 20 correspond respectively to parts 9 and 10 in FIG. 1.

Naturally, the pig 16 will detect the vibrations best when passing the crystal 15. The pig 16 may be provided with a component that can close a switch element in the box 14 when the pig approaches the said box and open it when the pig moves away from that box. The switch element operates the connection to the power supply in the box 14. The component in the pig may be a radiation source or a magnet. It is also possible for such a switch element to be located in box 6 of FIG. 1 and there to be operated by remote control, for instance by a coded vibration, when readings are to be taken.

In FIG. 3 the potential difference to be measured is connected with terminal 21. The signal is amplified by the direct current amplifier 22 and transmitted to the converter 23, which converts it into a low-frequency alternating current, such that the frequency has a specific value for a specific direct current. The frequency range may be, for instance, from 55 to 165 Hz.

An oscillator 24 and a pulse shaper 25 produce a high-frequency acoustic vibration, for instance with a frequency of 35 kHz. These pulses act as carrier wave and are modulated in modulator 26 with the low-frequency vibration of converter 23. With this modulator the carrier wave can be switched on and off by the low-frequency vibrations. The modulated signal goes to an oscillatory circuit 27, which contains a crystal 28 connected in parallel. The oscillatory circuit 27 is tuned to the carrier wave frequency. The crystal 28 transfers the vibrations to a part of the metal structure or to the water.

FIG. 4 again shows a tunable oscillatory circuit 31 with a crystal 32. The crystal 32 is located against a metal part of the structure or is in mechanical contact with the water to receive vibrarations that have been generated elsewhere in the metal structure. The signal goes via a preamplifier 33 to a selective amplifier 34 that only amplifies the frequency to which it is tuned. In a demodulator 35 the amplified signal is detected by rectification.

The signal that is representative of the potential of the metal structure (or, in fact, the potential difference between the metal structure and the reference electrode), is transmitted to recorder 37 via a selective low-frequency amplifier 36.

EXAMPLE

An ocean-going vessel was provided with sacrificial zinc electrodes. A vibration generator according to FIG. 3, which could be modulated, was installed against the outside of the ship's bottom. Near a cabin in the ship's superstructure the emitted vibration was received and processed by an installation according to FIG. 4.

During a 55 days' voyage with a 6 days' interruption in port the following results were obtained.

| Days | Place | Frequency Measured (Hz) | Potential in mV Against Zn | Potential in mV Against Saturated Calomel Electrode |
|---|---|---|---|---|
| 0 | at sea | 125 | + 250 | − 800 |
| 3 | at sea | 129 | + 290 | − 760 |
| 10 | at sea | 128 | + 280 | − 770 |
| 12 | at sea | 131 | + 310 | − 740 |
| 13 | at sea | 129 | + 290 | − 760 |
| 21 | at sea | 128 | + 280 | − 770 |
| 28 | in port | 128 | ± 280 | − 770 |
| 36 | at sea | 158 | + 540 | − 510 |
| 44 | at sea | 161 | + 570 | − 480 |
| 49 | at sea | 158 | + 540 | − 510 |

The results show that after 36 days the effect of the cathodic protection has decreased.

What is claimed is:

1. A method for measuring the cathodic protection potential of a structure at a remote location and transmitting the measurement to a convenient location, said method comprising:
   measuring the cathodic protection potential between the structure and a reference electrode at the remote point;
   converting the measured cathodic protection potential to a related frequency;
   producing an acoustic signal having said related frequency; and
   transmitting said acoustic signal to said convenient location.

2. The method of claim 1 wherein said acoustical signal comprises a carrier wave modulated by said related frequency.

3. The method of claim 2 wherein said acoustic signal has a frequency of 20–150 kilo-Hertz.

4. The method of claim 3 and in addition said related frequency being between 20–1000 Hertz.

5. The method of claim 1 wherein said cathodic protection potential is determined at a plurality of remote points, and the related frequency for each point is assigned a particular identifying code.

6. The method of claim 1 wherein the protected structure comprises an offshore oil structure and the acoustic signal is transmitted over a structural part of said structure and detected at a convenient location above the water level.

7. The method of claim 1 wherein said structure comprises a ship and the acoustical signal is transmitted through the hull of the ship and detected at a working location within said ship.

8. The method of claim 1 wherein said structure is a buried pipeline and the acoustical signal is transmitted through the pipeline to a convenient location.

9. The method of claim 8 and in addition passing a pig through pipeline, said pig detecting and recording said acoustic signal.

10. An apparatus for measuring the cathodic protection potential of a structure at a remote location and transmitting the measurement to a convenient location, said apparatus comprising:
   electrode means disposed at the remote location to measure the cathodic protection potential between said structure and a reference electrode;
   circuit means located at the remote location coupled to said electrode means and disposed to convert the measured cathodic protection potential to a related frequency signal;
   a transducer located at the remote location and coupled to said circuit means, said transducer being disposed to produce an acoustical signal related to the frequency signal;
   transmission means being disposed in an operable relationship with said transducer to transmit said acoustical signal from said remote location to said convenient location; and
   receiving means disposed at said convenient location for receiving said acoustical signal.

11. The apparatus of claim 10 wherein said structure comprises a buried pipeline, and said transducer is disposed to induce said acoustical signal in said pipeline.

12. The apparatus of claim 11 and in addition a pig disposed for travel through said pipeline, said receiving means being mounted in said pig to receive the acoustical signal induced in said pipeline.

13. The apparatus of claim 10 and in addition said circuit means including an oscillator for producing a carrier frequency and a modulator circuit coupled to said oscillator for modulating said carrier frequency in response to said related frequency signal, said modulator circuit being coupled to said transducer.

14. The apparatus of claim 13 wherein said receiving means includes an amplifier tuned to the frequency of said carrier frequency.

15. The apparatus of claim 10 wherein said structure comprises an offshore structure and said transmission means comprises at least one of the structural elements of said offshore structure.

* * * * *